(12) United States Patent
Esses

(10) Patent No.: US 10,130,731 B2
(45) Date of Patent: Nov. 20, 2018

(54) MOBILE DEVICE HOLDER AND POWERED AIR FRESHENER

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 0 days.

(21) Appl. No.: 15/470,400

(22) Filed: Mar. 27, 2017

(65) Prior Publication Data

US 2017/0232128 A1    Aug. 17, 2017

Related U.S. Application Data

(63) Continuation-in-part of application No. 14/736,520, filed on Jun. 11, 2015, now Pat. No. 9,610,376, which
(Continued)

(51) Int. Cl.
| | |
|---|---|
| *A61L 9/00* | (2006.01) |
| *A61L 9/03* | (2006.01) |
| *A61L 9/12* | (2006.01) |
| *H01R 31/02* | (2006.01) |
| *H02S 99/00* | (2014.01) |

(Continued)

(52) U.S. Cl.
CPC ............ *A61L 9/122* (2013.01); *A61L 9/03* (2013.01); *A61L 9/032* (2013.01); *H01R 24/28* (2013.01); *H01R 24/62* (2013.01); *H01R 31/02* (2013.01); *H02S 99/00* (2013.01); *A61L 2209/134* (2013.01); *H01R 2103/00* (2013.01); *H01R 2107/00* (2013.01)

(58) Field of Classification Search
CPC ............... A61L 9/00; A61L 9/03; A61L 9/037

USPC ........ 422/1, 5, 123, 125, 206; 392/386, 391, 392/394
See application file for complete search history.

(56) References Cited

U.S. PATENT DOCUMENTS

| | | | | |
|---|---|---|---|---|
| 5,499,748 A | * | 3/1996 | Iaia | B65D 23/003 222/180 |
| 6,102,660 A | * | 8/2000 | Lee | A61L 9/122 416/146 R |

(Continued)

FOREIGN PATENT DOCUMENTS

| | | |
|---|---|---|
| CN | 202641316 U | 1/2013 |
| DE | 202004002799 U | 6/2004 |

(Continued)

*Primary Examiner* — Monzer R Chorbaji
(74) *Attorney, Agent, or Firm* — Moritt Hock & Hamroff LLP; Bret P. Shapiro

(57) ABSTRACT

Technologies are generally described for apparatuses and methods relating to a mobile device holder and air freshener. The mobile device holder and air freshener may include a body, a fastening component, a removable cap, a flexible arm, and a mount. The fastening component may secure a mobile electronic device to the apparatus. The removable cap may allow scented material to be installed within the body. The fastening component may secure a mobile electronic device to the apparatus. The flexible arm may be coupled to the body at a first side and the mount on a second side. The mount and the flexible arm may support the mobile electronic device. The body may allow air that has entered the apparatus through a first vent of the apparatus to become scented and flow out of the apparatus through a second vent of the apparatus.

20 Claims, 12 Drawing Sheets

Related U.S. Application Data is a continuation-in-part of application No. 14/641,049, filed on Mar. 6, 2015, now Pat. No. 9,522,208, which is a continuation-in-part of application No. 14/463,176, filed on Aug. 19, 2014.

(51) Int. Cl.
  *H01R 24/28* (2011.01)
  *H01R 24/62* (2011.01)
  *H01R 103/00* (2006.01)
  *H01R 107/00* (2006.01)

(56) References Cited

U.S. PATENT DOCUMENTS

| | | | |
|---|---|---|---|
| 6,932,331 B1* | 8/2005 | Fan | A61L 9/127 |
| | | | 261/30 |
| 2005/0079113 A1* | 4/2005 | Selander | A61L 9/122 |
| | | | 422/306 |
| 2006/0078477 A1* | 4/2006 | Althouse | A01M 1/2044 |
| | | | 422/123 |
| 2013/0164178 A1 | 6/2013 | Carmichael | |
| 2013/0266486 A1 | 10/2013 | Wu | |
| 2014/0124594 A1* | 5/2014 | Hsiao | A61L 9/03 |
| | | | 239/135 |

FOREIGN PATENT DOCUMENTS

| | | |
|---|---|---|
| GB | 2062199 A | 5/1981 |
| KR | 2012015933 A | 11/2012 |

* cited by examiner

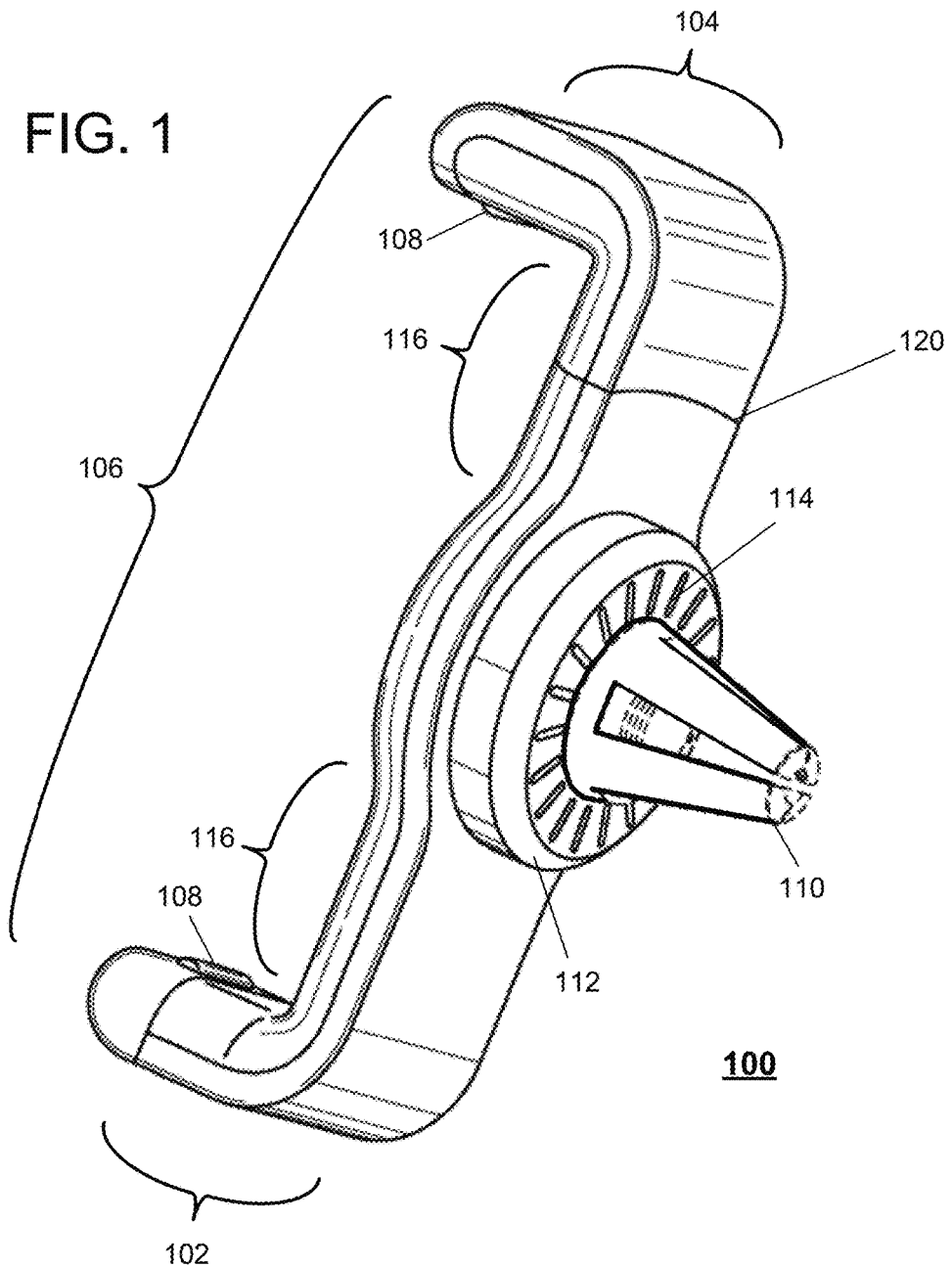

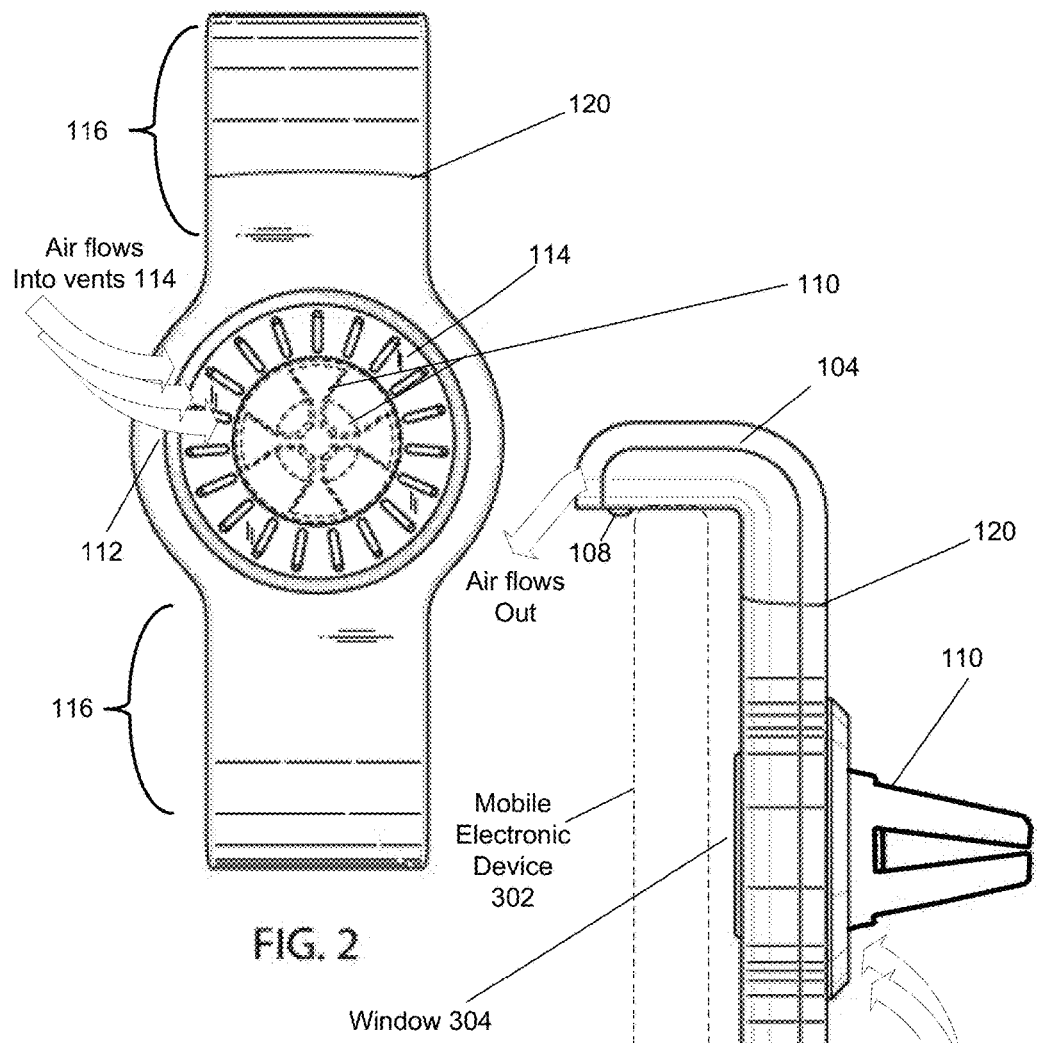

MOBILE DEVICE HOLDER AND POWERED AIR FRESHENER

CROSS REFERENCE TO RELATED APPLICATIONS

This application is a continuation in part under 35 U.S.C. § 120 of U.S. of application Ser. No. 14/736,520 filed on Jun. 11, 2015 which is a continuation in part under 35 U.S.C. § 120 of U.S. application Ser. No. 14/463,176 filed on Aug. 19, 2014 and application Ser. No. 14/641,049 filed on Mar. 6, 2015, the entirety of both applications are hereby incorporated by reference.

BACKGROUND

Air fresheners reduce or mask undesired odors and may emit pleasant odors. Air fresheners typically emit a pleasant odor in the form of a fragrance. Air fresheners include sprays, candles, oils, gels, and plug-ins.

SUMMARY OF THE INVENTION

In some examples, apparatuses are generally described. In some examples, the apparatuses may include a body. The body may be arranged so as to include an interior that is at least partially hollow. In some examples, the apparatuses may further include a removable cap. The removable cap may be removable to allow scented material to be installed within the interior. In some examples, the apparatuses may include a fastening component. The fastening component may be effective to secure a mobile electronic device to the apparatus. In some examples, the apparatuses may include a flexible arm. The flexible arm may be coupled to the body at a first side of the flexible arm. In some examples, the apparatuses may include a mount. The mount may be attached to a second side of the flexible arm. The mount and the flexible arm may be effective to support the mobile electronic device. The body may be further arranged so as to allow air that has entered the apparatus through a first vent on a first side of the body of the apparatus to become scented and flow out of the apparatus through a second vent on a second side of the body of the apparatus.

In yet other examples, apparatuses are generally described. In various examples, the devices may include a body. In some examples, the body may be arranged so as to include a first interior that is at least partially hollow. In other examples, the apparatuses may include a removable cap. In some examples, the removable cap may be removable to allow scented material to be installed within a second interior of the removable cap. In various other examples, the apparatuses may further include a fastening component. In some examples, the fastening component may be effective to secure a mobile electronic device to the apparatus. In various other examples, the apparatuses may include a flexible arm. The flexible arm may be coupled to the body at a first side of the flexible arm. In some examples, the apparatuses may include a mount. The mount may be attached to a second side of the flexible arm. The mount and the flexible arm may be effective to support the mobile electronic device. The body may be further arranged so as to allow air that has entered the apparatus through a first vent on a first side of the body of the apparatus to become scented through interaction with the scented material.

In other examples, methods to release fragrance from a scented material are generally described. In various examples, the methods may include placing the scented material inside an interior of an air freshener apparatus. In some examples, a fastening component of the air freshener apparatus may be effective to secure a mobile electronic device to the air freshener apparatus. In some examples, the methods may further include attaching the air freshener apparatus onto a surface or a vehicle cigarette lighter socket by a mount. In various other examples, the methods may include powering a fan with an electric current. The electric current may be provided from the mount. In some examples, the methods may further cause air to blow through the air freshener apparatus, by a fan, so that the air passes through a first vent into the air freshener apparatus. In some examples, air may interact with the scented material to produce scented air. For example, particulate matter from the scented material may be effective to mix with the air to create scented air. In some examples, the methods may further include causing, by the fan, the scented air to blow out of a second vent of the air freshener device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

FIG. 1 is an angled side perspective of a mobile device holder and air freshener;

FIG. 2 is a rear view of a mobile device holder and air freshener;

FIG. 3 is a side view of a mobile device holder and air freshener;

Figure 4:
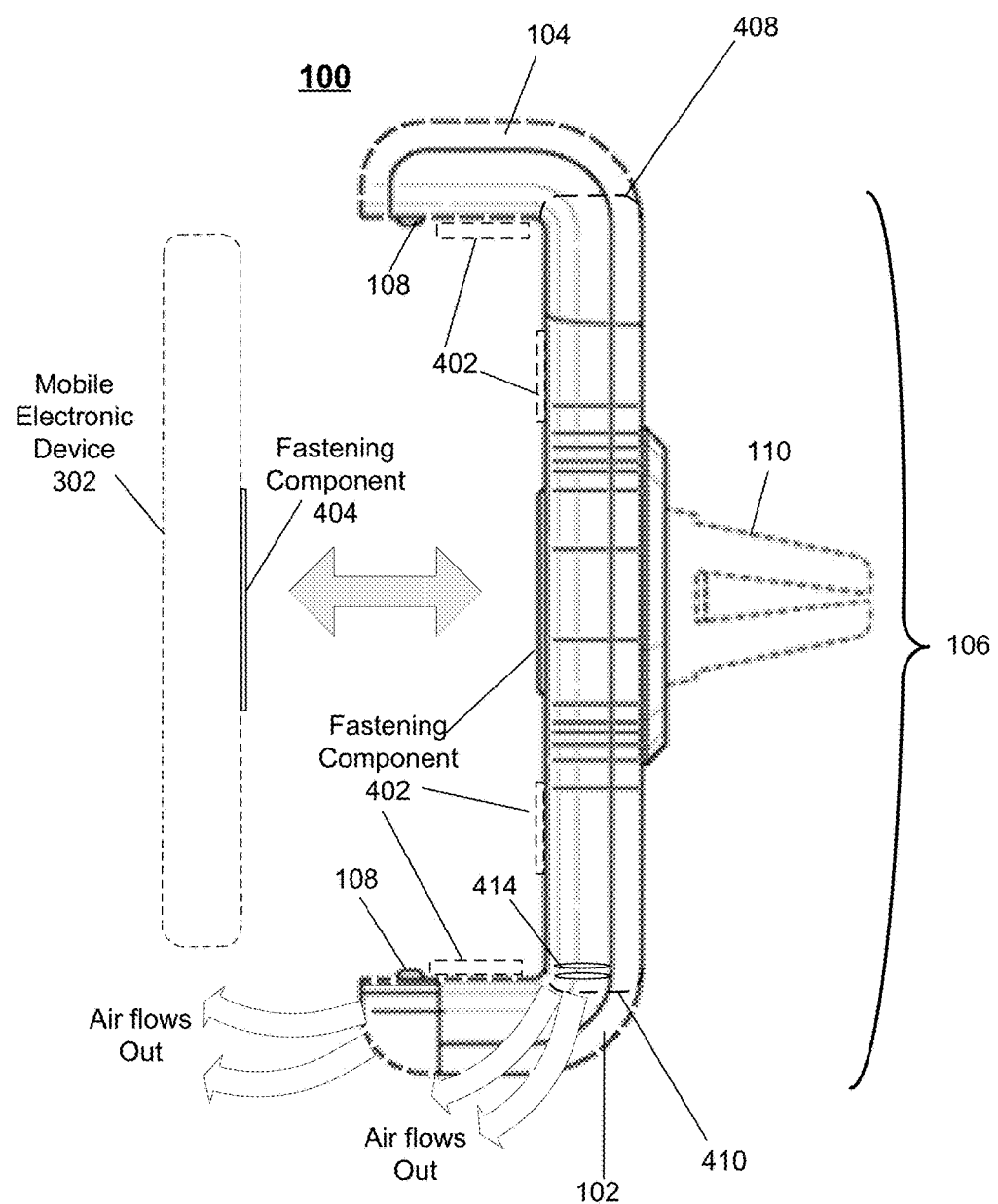
FIG. 4 is a side view of mobile device holder and air freshener 100 including fastening components.

all in accordance with one or more embodiments of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is an angled side perspective of a mobile device holder and air freshener in accordance with an embodiment of the invention. A mobile device holder and air freshener 100 may include a body 106, a bottom portion 102, a top portion 104, a removable cap 112, and/or a clip 110. Body 106 may include arms 116. Arms 116 may attach top portion 104 and bottom portion 102 to body 106 of mobile device holder and air freshener 100. In some examples, body 106, top portion 104, and/or bottom portion 102 may be arranged so as to include an interior that is at least partially hollow, such that air may flow through cavities within body 106, top portion 104, and/or bottom portion 102 of mobile device holder and air freshener 100. In some examples, top portion 104 and bottom portion 102 may be arranged at an angle that is perpendicular to or substantially perpendicular to arms 116. In various examples, bottom portion 102 may be effective to support a mobile electronic device such as a mobile phone, personal data assistant or tablet computing device. Top portion 104 and bottom portion 102 may include flanges 108. Flanges 108 may include raised material relative to an otherwise uniform, planar surface top portion 104 and/or bottom portion 102 of mobile device holder and air freshener 100. Flanges 108 may be configured to prevent a mobile electronic device installed or held between top portion 104 and bottom portion 102 of mobile device holder and air freshener 100 from falling out of mobile device holder and air freshener 100. In some other examples, a length of arms 116 may be adjustable. For example, a length of arms 116 may be adjusted axially such that top portion 104 and bottom portion 102 may be moved closer together and/or further apart from one another. In some examples, to be discussed in further detail below, arms 116 may be axially adjusted to hold and/or secure a mobile electronic device placed between top portion 104 and bottom portion 102. In some examples, flanges 108 may be effective to prevent a mobile electronic device installed in mobile device holder and air freshener 100 from becoming uninstalled or dislodged from between top portion 104 and bottom portion 102 of mobile device holder and air freshener 100. In some further examples, arms 116 may separate at one or more seams, such as seam 120, so that arms 116 may be adjusted. In some examples, seam 120 may be a line of division between an upper portion of arm 116 and a lower portion of arm 116.

Removable cap 112 may be removed from a coupling or connection to body 106 in order to install or replace scented material within body 106 and/or within an interior of removable cap 112 of mobile device holder and air freshener 100. In some examples, scented material may be a liquid oil, gel, aerosol, or solid material (such as ceramic, paper, etc.) infused with a fragrance. In some other examples, scented material may include scented oil encapsulated by a plastic ring or disc. The plastic ring or disc may include a membranous portion effective to allow scented oil to escape the ring or disc. The scented oil may evaporate, allowing scented particles to mix with the air to create scented air. In some examples, heating the oil may accelerate the evaporation of the oil. In some other examples, air flowing over the oil may accelerate evaporation of the oil. Fragrances may be any desirable fragrance, including fruit scents, new car smell, etc. Removable cap 112 may be arranged in such a way that removable cap 112 includes vents 114. Vents 114 may allow air to flow into and out of an interior of body 106. In some examples, air blown into and/or out of mobile device holder and air freshener 100 may be scented by scented material within body 106 and/or cap 112.

Removable cap 112 may include clip 110. Clip 110 may be an attachment mechanism and may be effective to clip onto various objects in order to secure mobile device holder and air freshener 100 to the objects. In an example, clip 100 may clip onto the vents of an automobile climate system or onto the blade-guards surrounding a home or office fan. Although depicted as being affixed to removable cap 112, clip 110 may be affixed to arms 116 and/or removable cap 112. In some further examples, clip 110 may be configured to rotate such that a mobile electronic device held by mobile device holder and air freshener 100 may be displayed horizontally, vertically, or at other angles relative to the ground. Air blowing from a fan of the automobile climate system or another fan may flow into or enter mobile device holder and air freshener 100 through vents 114. Air blowing into mobile device holder and air freshener 100 may become scented by interaction with scented material within body 106 and/or cap 112. In some examples, particulate matter from the scented material may mix with air blowing into body 106 and/or removable cap 112. Air flowing out of mobile device holder and air freshener 100 may be scented air, as particulate from a scented material within body 106 and/or removable cap 112 may have mixed with the air.

FIG. 2 depicts a rear view of mobile device holder and air freshener 100. Those components in FIG. 2 that are labelled identically to components of FIG. 1 may not be described again for the purposes of clarity and brevity. Arms 116 may be extended from body 106 and/or shortened into body 106 such that mobile electronic devices of different dimensions may be securely installed in mobile device holder and air freshener 100.

FIG. 3 depicts a side view of mobile device holder and air freshener 100. Those components in FIG. 3 that are labelled identically to components of FIGS. 1 and 2 may not be described again for the purposes of clarity and brevity. As depicted, an installed mobile electronic device 302 may be installed in mobile device holder and air freshener 100 between top portion 104 and bottom portion 102. In some examples, mobile electronic device 302 may be an electronic device such as a mobile phone, a tablet computing device, a global positioning system, an electronic reader or another electronic device. Arms 116 may be axially extended from body 106 and/or shortened into body 106, such that differently sized mobile electronic devices may be installed or secured between top portion 104 and bottom portion 102. For example, one or more of arms 116 may separate along seam 120. Flanges 108 may prevent installed mobile electronic device 302 from dislodging from mobile device holder and air freshener 100. Additionally, a rear portion of mobile electronic device 302 may be arranged along body 106 and/or a window 304 when mobile electronic device 302 is installed in mobile device holder and air freshener 100. In some examples, air flowing through vents 114 may flow through body 106 of mobile device holder and air freshener 100 and out of vents which may be included in top portion 104 and/or bottom portion 102 of mobile device holder and air freshener 100.

In some examples, window 304 may be arranged on a front portion of mobile device holder and air freshener 100. Window 304 may be formed from a transparent material such as plastic or glass. In some examples, window 304 may allow a user of mobile device holder and air freshener 100 to see an amount of scented material remaining inside an interior of mobile device holder and air freshener 100. In other examples, heat produced by mobile electronic device 302 may accelerate the release of particulate scented matter from scented material installed within removable cap 112 and/or body 106.

FIG. 4 depicts a side view of mobile device holder and air freshener 100. Those components in FIG. 4 that are labelled identically to components of FIGS. 1-3 may not be described again for the purposes of clarity and brevity. In some examples, mobile device holder and air freshener 100 may include a fastening component 402. In some examples, fastening component 402 may include a magnet, adhesive surface, or other attachment mechanism effective to secure mobile electronic device 302 to mobile device holder and air freshener 100. In some examples, a fastening component 404 may be attached to mobile electronic device 302 or to a case of mobile electronic device 302. In examples where fastening component 402 includes a magnet, fastening component 404 may include a metal effective to be attracted to the magnet. Conversely, in examples where fastening component 404 includes a magnet, fastening component 402 may include a metal effective to be attracted to the magnet. In some other examples, fastening components 402 and/or 404 may include attachment mechanisms such as VELCRO, polymer adhesive strips, straps, snaps, brackets, clips, etc. In general, fastening components 402 and 404 may include any mechanism effective to attach mobile electronic device 302 (or a case of mobile electronic device 302) to mobile device holder and air freshener 100.

In various examples where mobile device holder and air freshener 100 includes fastening components 402 and/or 404, mobile device holder and air freshener 100 may not include one or more of top portion 104 and bottom portion 102. Examples where mobile device holder and air freshener 100 does not include one or more of top portion 104 and bottom portion 102 are depicted in FIG. 4 using dashed lines 408 and 410 to show various alternate shapes of mobile device holder and air freshener 100. Portions of mobile device holder and air freshener 100 may be formed in such a way so as to include vents 414. Vents 414 may allow air blown into mobile device holder and air freshener 100 through vents 114 to escape from body 106 of mobile device holder and air freshener 100. In some examples, air escaping from vents 414 may be scented as a result of mixing with scented particulates released from a scented material installed within mobile device holder and air freshener 100. In various examples where mobile device holder and air freshener 100 includes top portion 104 and bottom portion 102, fastening component 402 may be located on one or more of top portion 104, bottom portion 102, and body 106.

Figure 5:
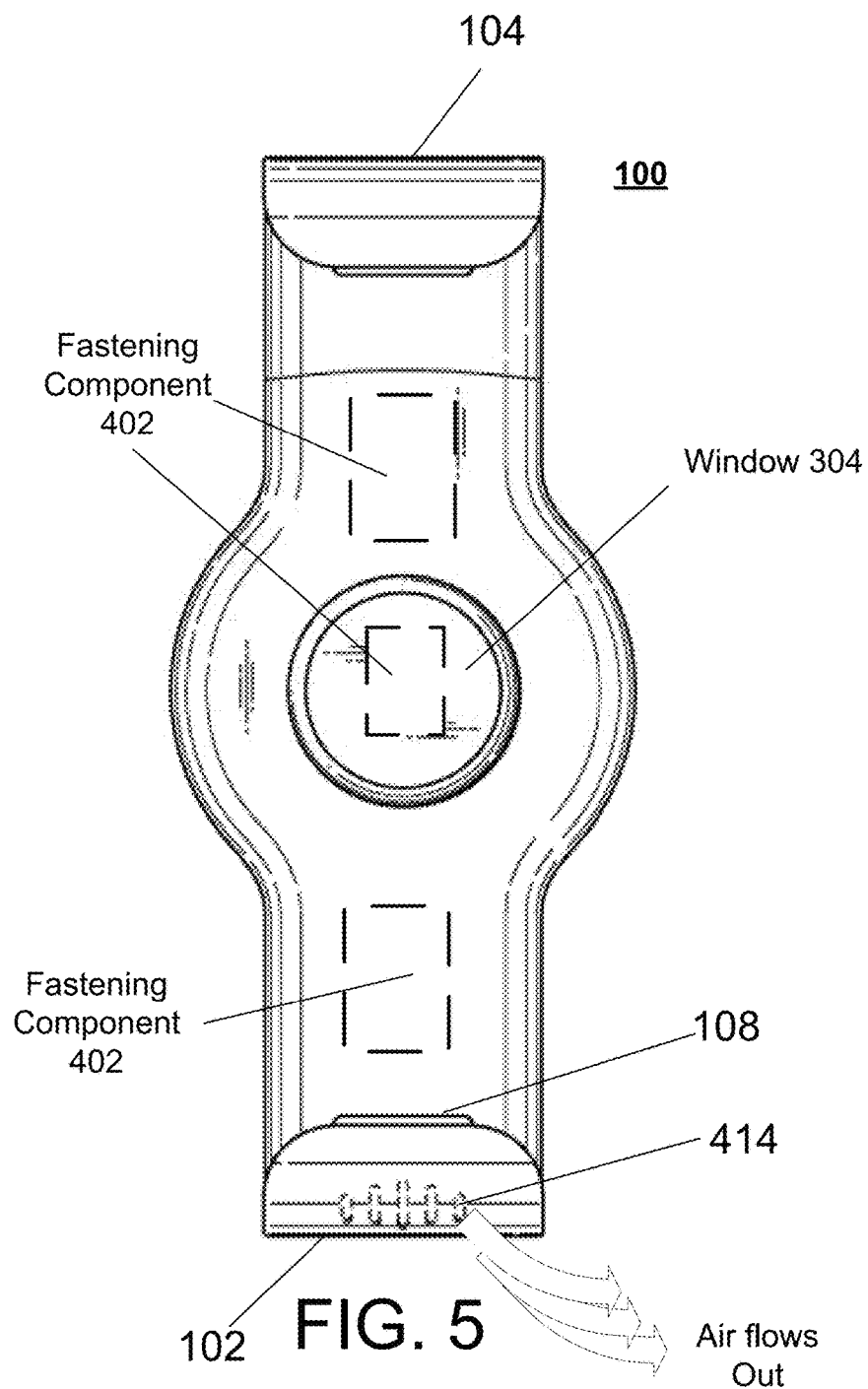
FIG. 5 is a front view of a mobile device holder and air freshener.

FIG. 5 depicts a front view of mobile device holder and air freshener 100. Those components in FIG. 5 that are labelled identically to components of FIGS. 1-4 may not be described again for the purposes of clarity and brevity. As depicted, mobile device holder and air freshener 100 may include window 304. As depicted, bottom portion 102 may be arranged in such a way as to include vents 414. Fastening components 402 may be included at various portions along mobile device holder and air freshener 100. Although two fastening components 402 are depicted in FIG. 5, more or fewer fastening components 402 may be used. Additionally, fastening components 402 may be placed anywhere on mobile device holder and air freshener 100. For example, in some embodiments, mobile device holder and air freshener 100 may be formed without window 304. In such an example, fastening component 402 may be positioned where window 304 is depicted as being positioned in FIG. 5. In some examples, mobile device holder and air freshener may include window 304 and one or more fastening components 402.

Figure 6:
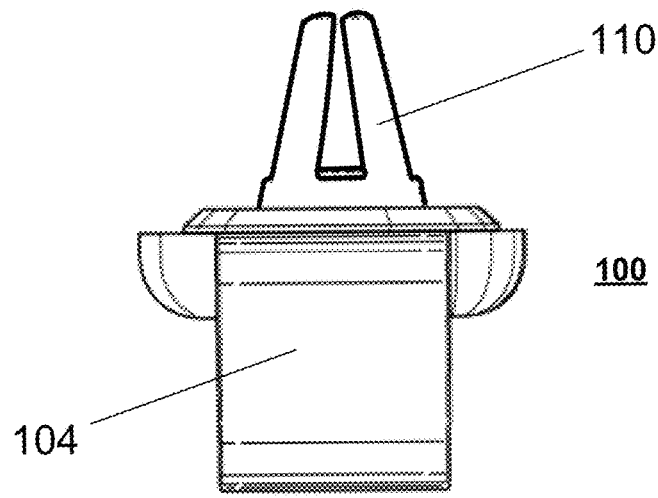
FIG. 6 is a top view of a mobile device holder and air freshener.
Figure 7:
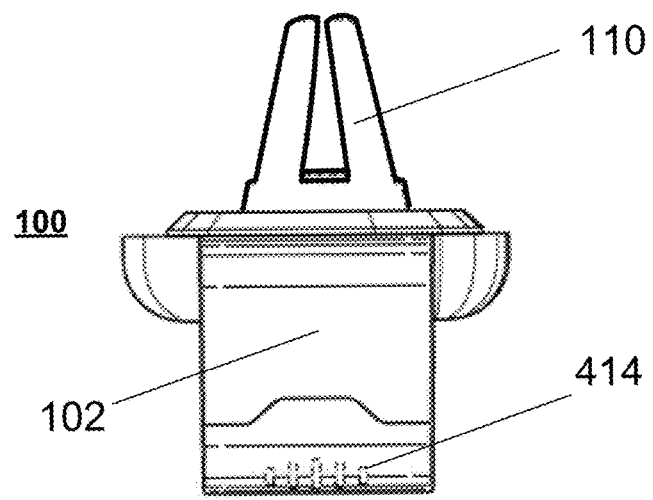
FIG. 7 is a bottom view of a mobile device holder and air freshener.

FIGS. 6 and 7 depict a top view and bottom view, respectively of mobile device holder and air freshener 100. Those components in FIGS. 6-7 that are labelled identically to components of FIGS. 1-5 may not be described again for the purposes of clarity and brevity. Although vents 414 are depicted as being included in bottom portion 102, vents 414 may be included in top portion 104, bottom portion 102 and top portion 104, or in other locations along mobile device holder and air freshener 100. In some examples, other locations may include arms 116 and/or body 106.

Figure 8:
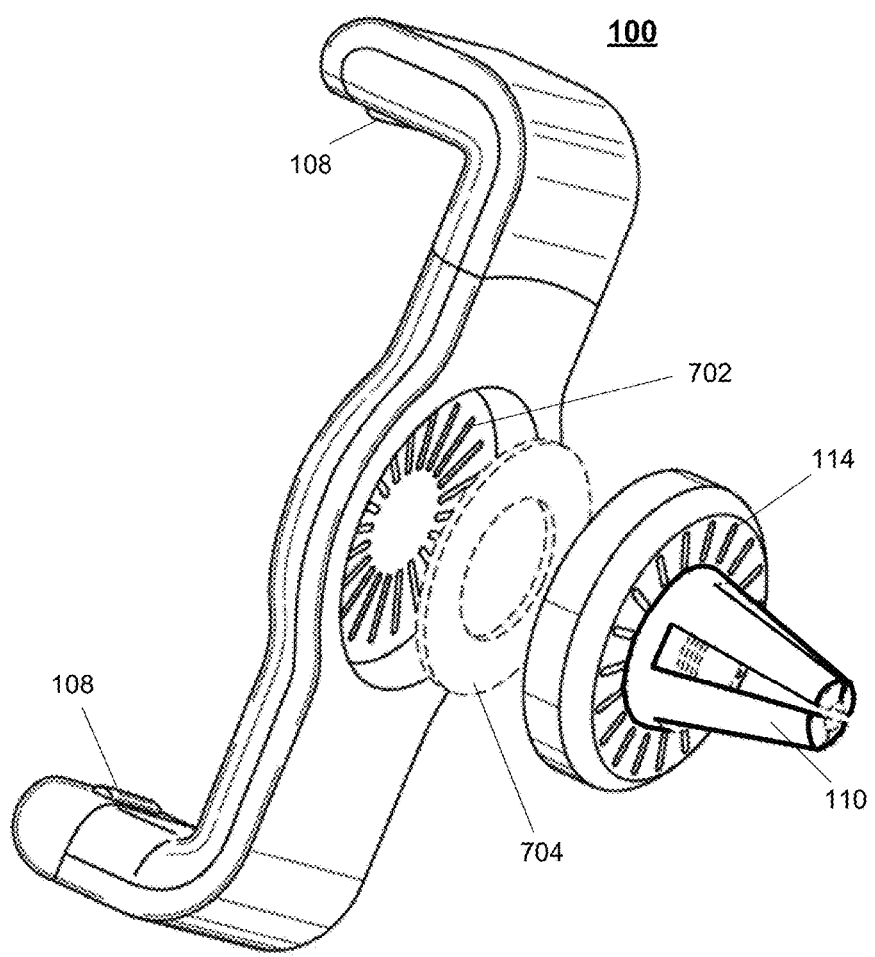
FIG. 8 is an angled side perspective, exploded view illustrating a body, a disk, and a cap enclosure of a mobile device holder and air freshener.

FIG. 8 depicts an angled side perspective, exploded view of mobile device holder and air freshener 100. Those components in FIG. 8 that are labelled identically to components of FIGS. 1-7 may not be described again for the purposes of clarity and brevity. As discussed, scented material may be installed within mobile device holder and air freshener 100. In an example, the scented material may include a scented material 704. In an example, scented material 704 may be in the shape of a flat ring or disc. In some examples, scented material 704 may be encapsulated by a capsule. In some examples, such a capsule may be ring or disc shaped. A capsule may include a membranous portion effective to allow scented oil to escape from the capsule. In some other examples, scented material 704 may take a different shape which may be optimized for installation and/or production of scented particulate within mobile device holder and air freshener 100. In some examples, body 106 of mobile device holder and air freshener 100 may be arranged in such a way as to include vents 702 in a front portion of mobile device holder and air freshener 100. Vents 702 may allow air and/or heat to flow into and out of mobile device holder and air freshener 100. In some examples, heat from a mobile electronic device installed within mobile device holder and air freshener 100 may flow through vents 702 and may increase an amount of particulate released from scented material 704.

Figure 9:
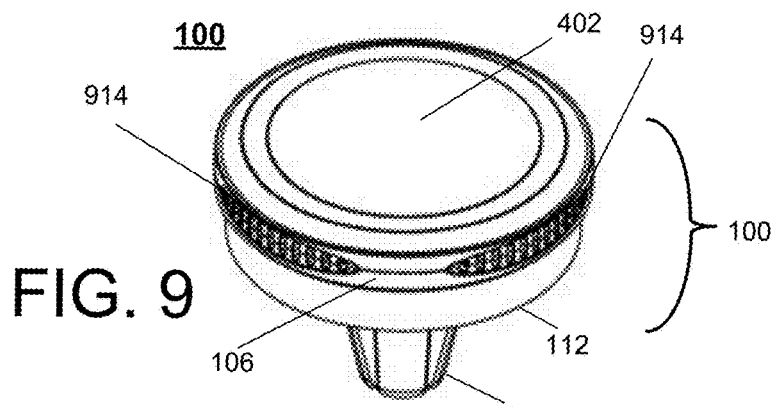
FIG. 9 is a front perspective view of a mobile device holder and air freshener including a fastening component.

FIG. 9 depicts front perspective view of mobile device holder and air freshener 100 including fastening component 402. Those components in FIG. 9 that are labelled identically to components of FIGS. 1-8 may not be described again for the purposes of clarity and brevity. As depicted, body 106 of mobile device holder and air freshener 100 may be formed in a substantially circular or semi-circular shape. In some other examples, body 106 may be formed so as to resemble various polygons or combinations of polygons and curved surfaces from the front perspective view depicted in FIG. 9. In some examples, mobile device holder and air freshener 100 may be formed without arms (such as arms 116 described in FIG. 1), a top portion (such as top portion 104 described in FIG. 1), and/or a bottom portion (such as bottom portion 102 described in FIG. 1). Fastening component 402 may be formed on or within a surface of mobile device holder and air freshener 100 such that a mobile device may be secured to mobile device holder and air freshener 100. In various examples, fastening component 402 may be made of a polymer material which may adhere or otherwise cling to a surface of a mobile device or mobile device case. In other examples and as described previously, fastening component 402 may be a magnet effective to secure a mobile device or a case of a mobile device to mobile device holder and air freshener 100. Conversely, fastening component 402 may be metal material such that a magnet attached to a mobile device or a case of a mobile device may be secured to mobile device holder and air freshener 100.

Mobile device holder and air freshener 100 may include one or more vents 914. In some examples, removable cap 112 may be removed from a coupling or connection to body 106 in order to install or replace scented material within body 106 and/or within an interior of removable cap 112 of mobile device holder and air freshener 100. In some examples, vents 914 may be positioned around the perimeter of body 106 or removable cap 112. In various examples, vents 914 may allow air blown into mobile device holder and air freshener 100 through vents 114 (depicted in FIG. 10) or through other vents or ingress points to escape from mobile device holder and air freshener 100. In some examples, air escaping from vents 914 may be scented as a result of mixing with scented particulates released from a scented material installed within mobile device holder and air freshener 100.

Mobile device holder and air freshener 100 may include clip 110. Clip 110 may be effective to clip onto various objects in order to secure mobile device holder and air freshener 100 to the objects. In an example, clip 110 may clip onto the vents of an automobile climate system or onto the blade-guards surrounding a home or office fan. In various examples, clip 110 may be coupled or otherwise attached to body 106. In examples where clip 110 is coupled to body 106, removable cap 112 may be removed from mobile device holder and air freshener 100 while clip 110 remains coupled to body 106. In various other examples, clip 110 may be coupled to removable cap 112, and may be removed from body 106 together with removable cap 112.

Figure 10:
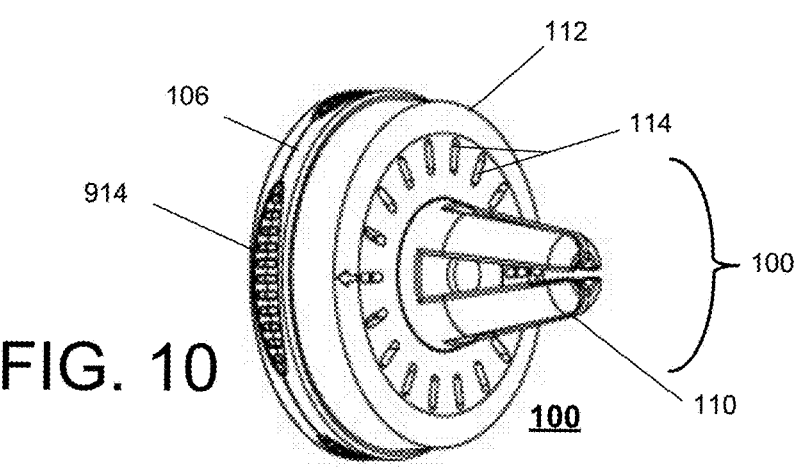
FIG. 10 is a bottom perspective view of a mobile device holder and air freshener including vents.

FIG. 10 depicts a bottom perspective view of mobile device holder and air freshener 100 including vents 914. Those components in FIG. 10 that are labelled identically to components of FIGS. 1-9 may not be described again for the purposes of clarity and brevity. In some examples, removable cap 112 of mobile device holder and air freshener 100 may include vents 114. Vents 114 may allow air to flow into and out of an interior of body 106 or removable cap 112. In some examples, air blown into and/or out of mobile device holder and air freshener 100 may be scented by scented material within body 106. Vents 914 may allow air blown into mobile device holder and air freshener 100 through vents 114 to escape from body 106 of mobile device holder and air freshener 100. In some examples, air escaping from vents 914 may be scented as a result of mixing with scented particulates released from a scented material installed within mobile device holder and air freshener 100.

Figure 11:
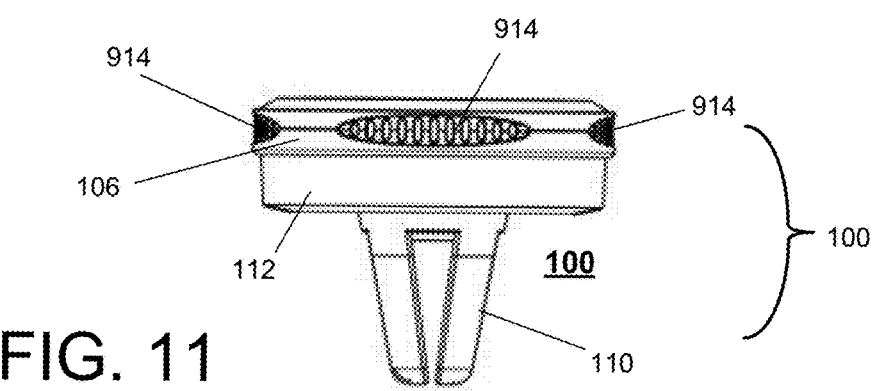
FIG. 11 is a side view of a mobile device holder and air freshener including vents.

FIG. 11 depicts a side view of mobile device holder and air freshener 100 including vents 914. Those components in FIG. 11 that are labelled identically to components of FIGS. 1-10 may not be described again for the purposes of clarity and brevity. As depicted, mobile device holder and air freshener 100 may include one or more vents 914, clip 110, removable cap 112, and body 106.

Figure 12:
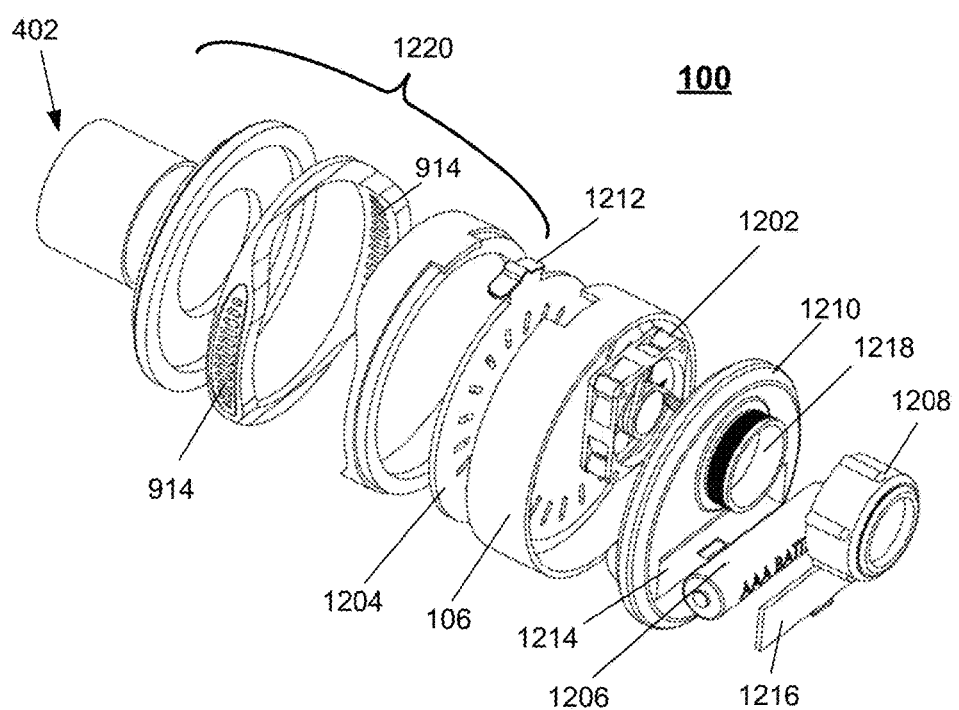
FIG. 12 is an exploded, side perspective view of mobile device holder and air freshener including a fan.

FIG. 12 depicts an exploded, side perspective view of mobile device holder and air freshener 100 including a fan 1202. Those components in FIG. 12 that are labelled identically to components of FIGS. 1-11 may not be described again for the purposes of clarity and brevity.

Mobile device holder and air freshener 100 may include a removable cap 1220. Removable cap 1220 may be removable from body 106 and/or from a vented plate 1204 so that scented material may be installed within mobile device holder and air freshener 100. In various examples, removable cap 1220 may include one or more component pieces or portions. For example, as depicted in FIG. 12 removable cap 1220 may include a portion which may include fastening component 402 and a different portion which may include vents 914. In some other examples, removable cap 1220 may be a solid piece.

In some examples, a vented plate 1204 may be disposed between removable cap 112 and body 106. Vented plate 1204 may be arranged to support or hold scented material placed on vented plate 1204. Scented material may be installed, replaced, or otherwise positioned on vented plate 1204 when removable cap 1220 is removed from body 106. In some examples, vents formed in vented plate 1204 may allow air to flow between removable cap 1220 and body 106.

In some examples, vented plate 1204 may include a clasp 1212. Clasp 1212 may be used to lock or secure removable cap 1220 to body 106. Conversely, clasp 1212 may be activated in order to remove removable cap 1220 from body 106. Although clasp 1212 is depicted on vented plate 1204 in FIG. 12, clasp 1212 may be formed on body 106 and/or removable cap 1220.

In some examples, mobile device holder and air freshener 100 may include a fan 1202. Fan 1202 may be an electric motor and may include one or more blades which may be effective to displace air when fan 1202 is activated. Fan 1202 may be effective to blow air through vents of vented plate 1204 and out of vents 914. In some examples, air blown by fan 1202 may become scented as a result of mixing with scented particulates released from a scented material installed within mobile device holder and air freshener 100. In various examples, mobile device holder and air freshener 100 may include a power supply 1206 which may be effective to power fan 1202. In some examples, power supply 1206 may include one or more batteries, power electronics, and/or a power cable.

In the example device depicted in FIG. 12, mobile device holder and air freshener 100 may include a base 1210. Base 1210 may be effective to attach to body 106. Additionally, base 1210 may be formed in such a way as to include a compartment 1214. In some examples, compartment 1214 may be effective to hold power supply 1206. In various examples, cover 1216 may be effective to cover and/or enclose compartment 1214. In some examples, base 1210 may be formed in such a way as to include a vent 1218. Vent 1218 may allow fan 1202 to pull air into mobile device holder and air freshener 100.

Mobile device holder and air freshener 100 may include a collar 1208. Collar 1208 may be effective to attach mobile device holder and air freshener 100 to another object. For example, collar 1208 may be effective to attach mobile device holder and air freshener 100 to clip 110 (depicted in FIGS. 1-4 and 6-11) or to a flexible arm, as will be described in further detail below.

Figure 13:
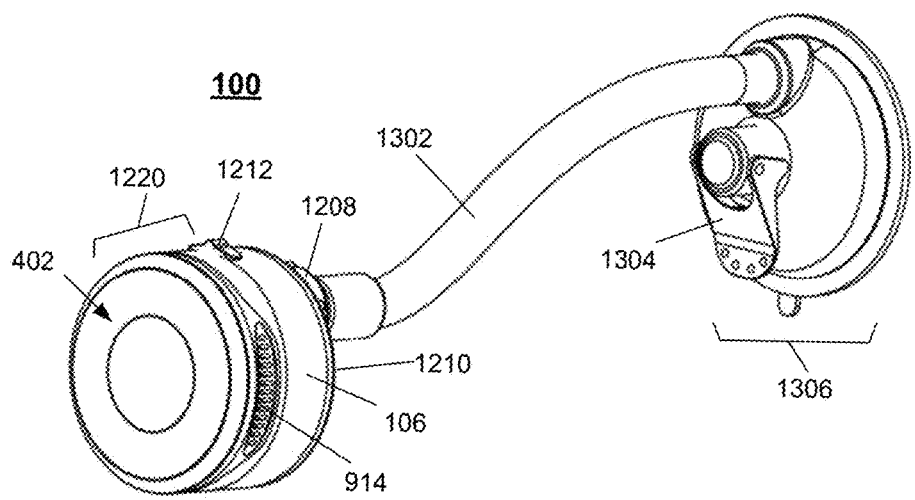
FIG. 13 is a side perspective view of mobile device holder and air freshener including a flexible arm and mount.
Figure 14:
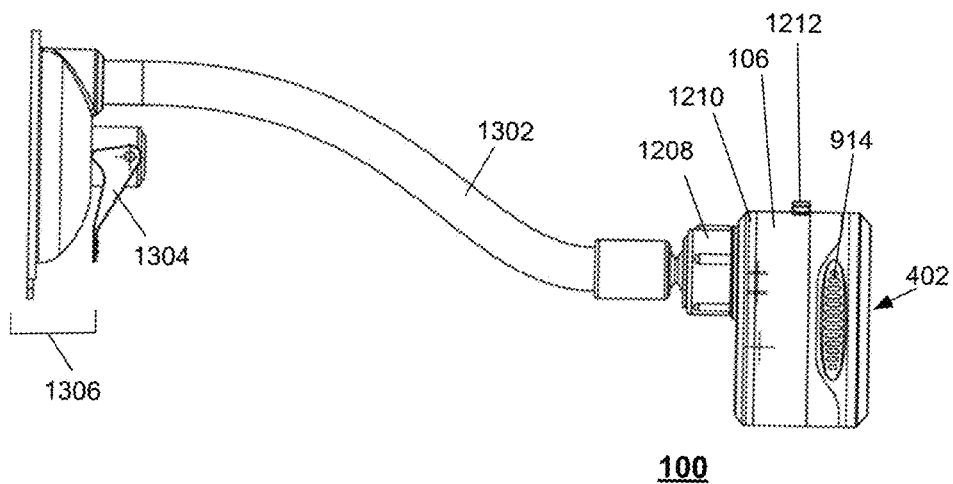
FIG. 14 is a side view of the mobile device holder and air freshener of FIG. 13.

FIG. 13 depicts a side perspective view of mobile device holder and air freshener 100 including a flexible arm 1302 and a mount 1306. FIG. 14 depicts a side view of the mobile device holder and air freshener 100 of FIG. 13. Those components of FIGS. 13 and 14 that are labelled identically to components of FIGS. 1-12 may not be described again for the purposes of clarity and brevity.

In some examples, mobile device holder and air freshener 100 may include a mount 1306. Mount 1306 may be an attachment device and may be effective to secure mobile device holder and air freshener 100 to a surface. In various examples, mount 1306 may allow mobile device holder and air freshener 100 to be secured to glass, wood, plastic, composite, and/or other materials. In some examples, mount 1306 may use suction as a means to secure mobile device holder and air freshener 100 to a surface. In examples where mount 1306 uses suction to secure mobile device holder and air freshener 100 to a surface, mount 1306 may include a suction cup and a lever 1304. Lever 1304 may be effective to engage and disengage suction in mount 1306 so that mount 1306 of mobile device holder and air freshener 100 may be secured to a surface.

In some examples, collar 1208 of mobile device holder and air freshener 100 may be effective to couple to flexible arm 1302. Flexible arm 1302 may be flexible so that a user may position mobile device holder and air freshener 100 when mount 1306 is mounted to a surface. For example, mount 1306 may be mounted to the interior windshield of an automobile. A user may adjust flexible arm 1302 so that the user may comfortably view a mobile device fastened or secured to mobile device holder and air freshener 100 by fastening component 402.

Figure 15:
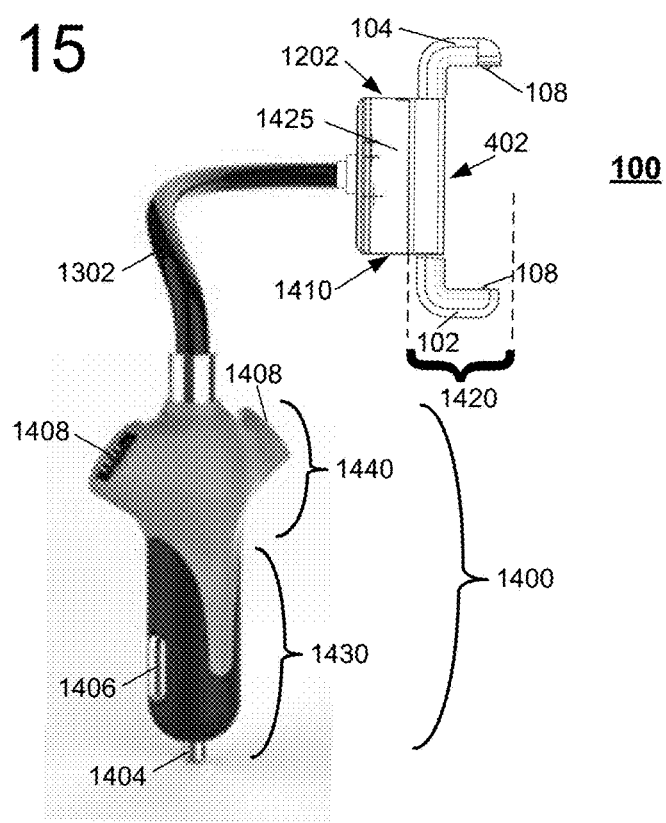
FIG. 15 is a side perspective view of mobile device holder and powered air freshener including a flexible arm and dual USB car charger mount.

FIG. 15 is a side perspective view of mobile device holder and powered air freshener including a flexible arm and dual USB car charger mount in accordance with an embodiment of the invention. Those components of FIG. 15 that are labelled identically to components of FIGS. 1-14 may not be described again for the purposes of clarity and brevity.

In some examples, mobile device holder and air freshener 100 may include flexible arm 1302 and a car charger mount 1400. Car charger mount 1400 may include an insertion section 1430 and a top section 1440. Insertion section 1430 may include an anode electrode 1404 extending axially from insertion section 1430 and at least one cathode electrode 1406 extending radially from the sides of insertion section 1430. Insertion section 1430 including anode electrode 1404 and cathode electrode 1406, may be arranged such that device holder and air freshener 100 may be plugged into a cigarette lighter socket, such as a vehicle cigarette lighter socket, with the anode electrode 1404 and the cathode electrode 1406 aligning and connecting to the electrodes of the vehicle cigarette lighter socket, respectively. Insertion section 1430 inserted into a vehicle cigarette lighter socket may secure mobile device holder and air freshener 100 to vehicle cigarette lighter socket. The current provided by the vehicle cigarette lighter socket may be direct current and may be 12 volts. Current provided by the vehicle cigarette lighter socket when insertion section 1430 is inserted into the vehicle cigarette lighter socket may be effective to power a fan 1202, or an electronic heating device 1410 within mobile device holder and air freshener 100. Heat from electronic heating device 1410 may increase an amount of particulate released from a scented material installed within mobile device holder and air freshener 100.

Top section 1440 may include ports 1408. Ports 1408 may be universal serial bus (USB) ports and may be powered by current provided by the vehicle cigarette lighter socket when insertion section 1430 is inserted into the vehicle cigarette lighter socket. USB ports 1408 may function to supply power to connected USB cables for powering and/or charging devices attached to a connected USB cable.

In some examples, car charger mount 1400 of mobile device holder and air freshener 100 may be effective to couple to flexible arm 1302. Flexible arm 1302 may be flexible so that a user may position mobile device holder and air freshener 100 when car charger mount 1400 is inserted and secured in the vehicle cigarette lighter socket. A user may adjust flexible arm 1302 so that the user may comfortably view a mobile device fastened or secured to mobile device holder and air freshener 100 by fastening component 402 and/or flanges 108 of arms 102 and 104 respectively.

Mobile device holder and air freshener 100 may include a removable cap 1420 and a base 1425. Removable cap 1420 may be removable from base 1425 so that scented material may be installed within mobile device holder and air freshener 100. In various examples, removable cap 1420 may include one or more component pieces or portions. For example, as depicted in FIG. 15 removable cap 1420 may include fastening component 402, arms 102 and 104, and flanges 108 of arms 102 and 104.

Figure 16:
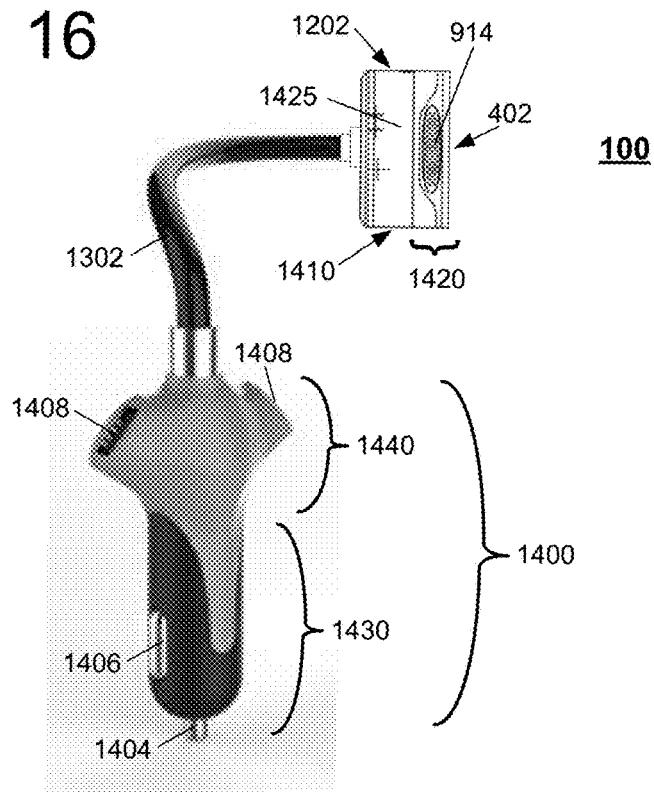
FIG. 16 is a side perspective view of mobile device holder and powered air freshener including a flexible arm and dual USB car charger mount.

FIG. 16 is a side perspective view of mobile device holder and powered air freshener including a flexible arm and dual USB car charger mount in accordance with an embodiment of the invention. Those components of FIG. 16 that are labelled identically to components of FIGS. 1-15 may not be described again for the purposes of clarity and brevity.

In some examples, mobile device holder and air freshener 100 may include flexible arm 1302 and car charger mount 1400. Car charger mount 1400 may include insertion section 1430 and top section 1440. Insertion section 1430 may include anode electrode 1404 extending axially from insertion section 1430 and at least one cathode electrode 1406 extending radially from the sides of insertion section 1430. Insertion section 1430 including anode electrode 1404 and cathode electrode 1406, may be arranged such that mobile device holder and air freshener 100 may be plugged into a cigarette lighter socket, such as a vehicle cigarette lighter socket, with the anode electrode 1404 and the cathode electrode 1406 aligning and connecting to the electrodes of the vehicle cigarette lighter socket respectively. Insertion section 1430 inserted into vehicle cigarette lighter socket may secure mobile device holder and air freshener 100 to vehicle cigarette lighter socket. The current provided by the vehicle cigarette lighter socket may be direct current and may be 12 volts. Current provided by the vehicle cigarette lighter socket when insertion section 1430 is inserted into the vehicle cigarette lighter socket may be effective to power a fan 1202, or an electronic heating device 1410 within mobile device holder and air freshener 100. Fan 1202 may be effective to blow air including scented particles released from a scented material installed within air freshener 100 out of vents 914. Heat from electronic heating device 1410 may increase an amount of particulate released from a scented material installed within mobile device holder and air freshener 100.

Top section 1440 may include ports 1408. Ports 1408 may be universal serial bus (USB) ports and may be powered by current provided by the vehicle cigarette lighter socket when insertion section 1430 is inserted into the vehicle cigarette lighter socket. USB ports 1408 may function to supply power to connected USB cables for powering and/or charging devices attached to a connected USB cable.

In some examples, car charger mount 1400 of mobile device holder and air freshener 100 may be effective to couple to flexible arm 1302. Flexible arm 1302 may be flexible so that a user may position mobile device holder and air freshener 100 when car charger mount 1400 is inserted and secured in the vehicle cigarette lighter socket. A user may adjust flexible arm 1302 so that the user may comfortably view a mobile device fastened or secured to mobile device holder and air freshener 100 by fastening component 402.

Mobile device holder and air freshener 100 may include a removable cap 1420 and a base 1425. Removable cap 1420 may be removable from base 1425 so that scented material may be installed within mobile device holder and air freshener 100. In various examples, removable cap 1420 may include one or more component pieces or portions. For example, as depicted in FIG. 16 removable cap 1420 may include fastening component 402 and vents 914.

Figure 17:
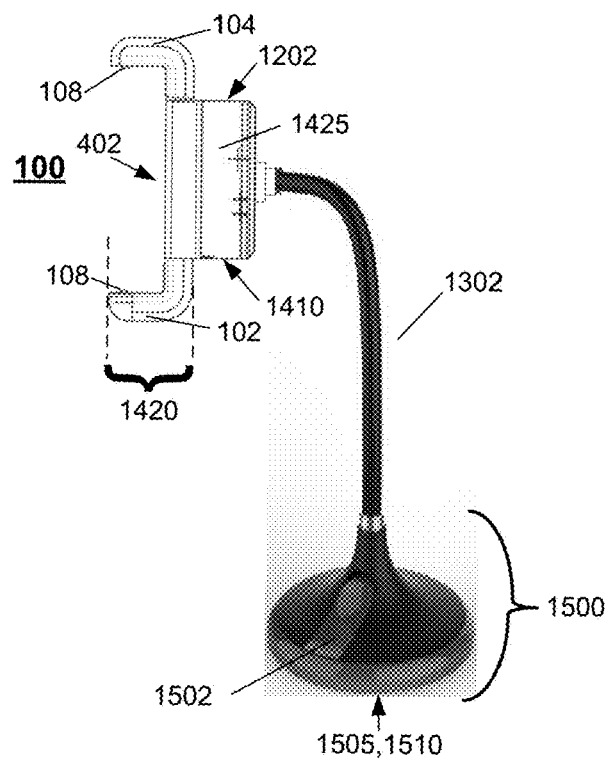
FIG. 17 is a side perspective view of mobile device holder and powered air freshener including a flexible arm and solar mount.

FIG. 17 is a side perspective view of mobile device holder and powered air freshener including a flexible arm and solar mount in accordance with an embodiment of the invention. Those components of FIG. 17 that are labelled identically to components of FIGS. 1-16 may not be described again for the purposes of clarity and brevity.

In some examples, mobile device holder and air freshener 100 may include flexible arm 1302 and a solar mount 1500. Solar mount 1500 may be an attachment device and may be effective to secure mobile device holder and air freshener 100 to a surface. In various examples, solar mount 1500 may allow mobile device holder and air freshener 100 to be secured to glass, wood, plastic, composite, and/or other materials. In some examples, solar mount 1500 may include a suction cup 1510 to secure mobile device holder and air freshener 100 to a surface. In examples where solar mount 1500 uses suction cup 1510 to secure mobile device holder and air freshener 100 to a surface; solar mount 1500 may include suction cup 1510 and a lever 1502. Lever 1502 may be effective to engage and disengage suction cup 1510 in solar mount 1500 so that solar mount 1500 of mobile device holder and air freshener 100 may be secured to a surface.

As described in more detail below, solar mount 1500 may include solar cell 1505. Solar cell 1505 may, upon being incident by incident light, generate an electric current. Current provided by solar cell 1505 may be effective to power fan 1202, or electronic heating device 1410 within device holder and air freshener 100. Heat from electronic heating device 1410 may increase an amount of particulate released from a scented material installed within mobile device holder and air freshener 100.

In some examples, solar mount 1500 may include a disposable battery or a built in rechargeable battery. Current provided by disposable battery or a built in rechargeable battery may be effective to power fan 1202, or electronic heating device 1410 within device holder and air freshener 100.

In some examples, solar mount 1500 of mobile device holder and air freshener 100 may be effective to couple to flexible arm 1302. Flexible arm 1302 may be flexible so that a user may position mobile device holder and air freshener 100 when solar mount 1500 is secured to a surface, such as a windshield of the car. A user may adjust flexible arm 1302 so that the user may comfortably view a mobile device fastened or secured to mobile device holder and air freshener 100 by fastening component 402 and/or flanges 108 of arms 102 and 104 respectively.

Mobile device holder and air freshener 100 may include a removable cap 1420 and a base 1425. Removable cap 1420 may be removable from base 1425 so that scented material may be installed within mobile device holder and air freshener 100. In various examples, removable cap 1420 may include one or more component pieces or portions. For example, as depicted in FIG. 17 removable cap 1420 may include fastening component 402, arms 102 and 104, and flanges 108 of arms 102 and 104.

Figure 18:
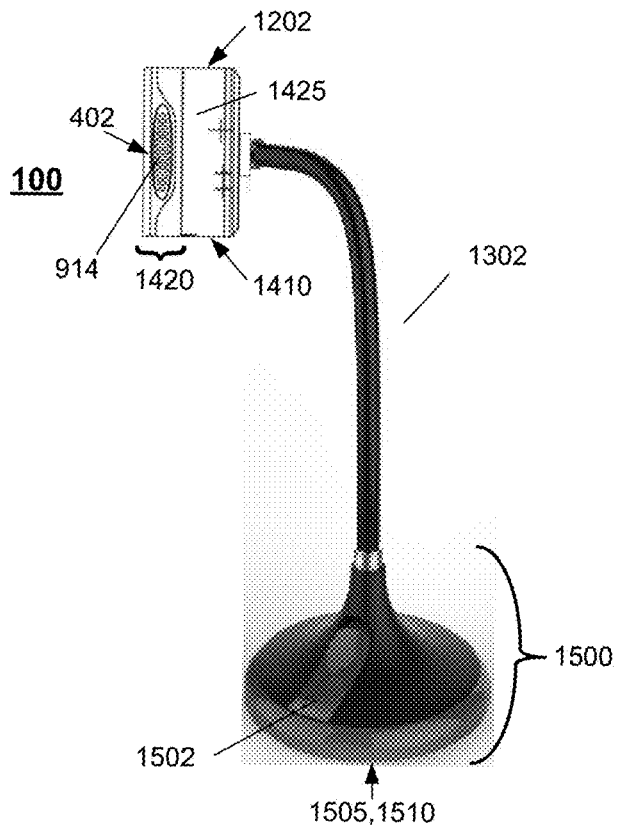
FIG. 18 is a side perspective view of mobile device holder and powered air freshener including a flexible arm and solar mount.

FIG. 18 is a side perspective view of mobile device holder and powered air freshener including a flexible arm and solar mount in accordance with an embodiment of the invention. Those components of FIG. 18 that are labelled identically to components of FIGS. 1-17 may not be described again for the purposes of clarity and brevity.

In some examples, mobile device holder and air freshener 100 may include flexible arm 1302 and a solar mount 1500. Solar mount 1500 may be an attachment device and may be effective to secure mobile device holder and air freshener 100 to a surface. In various examples, solar mount 1500 may allow mobile device holder and air freshener 100 to be secured to glass, wood, plastic, composite, and/or other materials. In some examples, solar mount 1500 may include suction cup 1510 to secure mobile device holder and air freshener 100 to a surface. In examples where solar mount 1500 uses suction cup 1510 to secure mobile device holder and air freshener 100 to a surface; solar mount 1500 may include suction cup 1510 and a lever 1502. Lever 1502 may be effective to engage and disengage suction cup 1510 in solar mount 1500 so that solar mount 1500 of mobile device holder and air freshener 100 may be secured to a surface.

Solar mount 1500 may include solar cell 1505. Solar cell 1505 may, upon being incident by incident light, generate an electric current. Current provided by solar cell 1505 may be effective to power a fan 1202, or an electronic heating device 1410 within device holder and air freshener 100. Fan 1202 may be effective to blow air including scented particles released from a scented material installed within air freshener 100 out of vents 914. Heat from electronic heating device 1410 may increase an amount of particulate released from a scented material installed within mobile device holder and air freshener 100.

In some examples, solar mount 1500 may include a disposable battery or a built in rechargeable battery. Current provided by disposable battery or a built in rechargeable battery may be effective to power fan 1202, or electronic heating device 1410 within device holder and air freshener 100.

In some examples, solar mount 1500 of mobile device holder and air freshener 100 may be effective to couple to flexible arm 1302. Flexible arm 1302 may be flexible so that a user may position mobile device holder and air freshener 100 when car charger mount 1500 is secured to a surface, such as a windshield of the car. A user may adjust flexible arm 1302 so that the user may comfortably view a mobile device fastened or secured to mobile device holder and air freshener 100 by fastening component 402.

Mobile device holder and air freshener 100 may include a removable cap 1420 and a base 1425. Removable cap 1420 may be removable from base 1425 so that scented material may be installed within mobile device holder and air freshener 100. In various examples, removable cap 1420 may include one or more component pieces or portions. For example, as depicted in FIG. 16 removable cap 1420 may include fastening component 402 and vents 914.

Figure 19:
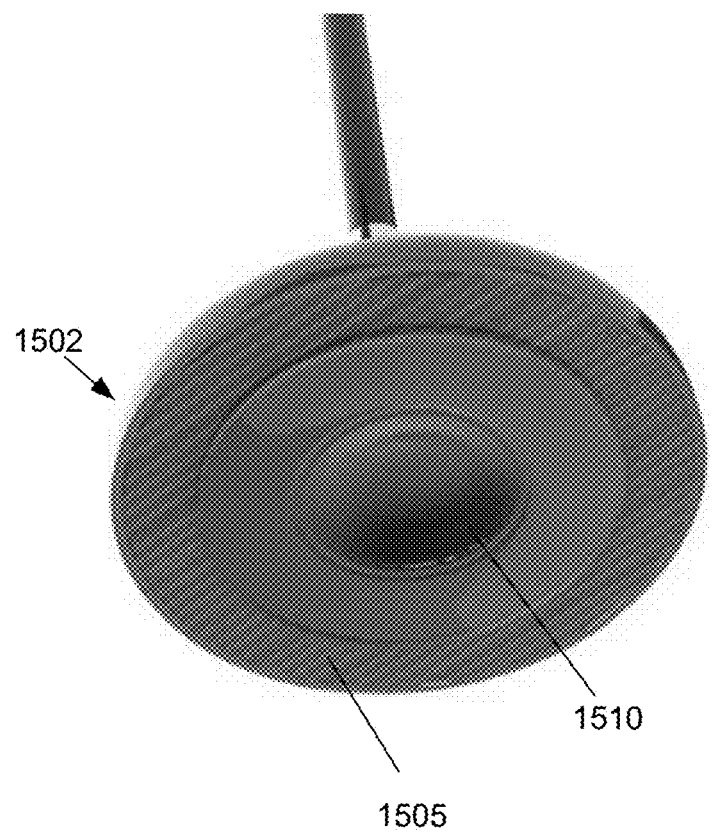
FIG. 19 is a bottom perspective view of a solar mount.

FIG. 19 is a bottom perspective view of a solar mount in accordance with an embodiment of the invention. Those components of FIG. 19 that are labelled identically to components of FIGS. 1-18 may not be described again for the purposes of clarity and brevity.

Solar mount 1500 may include solar cell 1505, suction cup 1510, and lever 1502. Solar mount may be secured onto a surface of, for example, a windshield of a car by suction cup 1510 and lever 1502. Solar mount 1500, attached to a windshield of a car may receive incident light to solar cell 1505. Solar cell 1505, upon being incident by incident light, may convert electromagnetic radiation in incident light into an electric current. Current generated by solar cell 1505 may be effective to power a fan 1202, or an electronic heating device 1410 within device holder and air freshener 100.

Among other potential benefits, a mobile device holder and air freshener may be secured to a cigarette socket or other surface in an automobile. A mobile electronic device held by the mobile device holder and air freshener may be easily visible to a driver of an automobile as a result of the mobile device holder and air freshener being conveniently positioned and/or rotated to be within a driver's field of vision. In some other examples, a fan installed within the mobile device holder and air freshener may allow air to blow through the mobile device holder and air freshener. Air blown through the mobile device holder and air freshener may become scented by scented material within the mobile device holder and air freshener. Thus, the mobile device holder and air freshener may allow a driver to view a mobile phone in a convenient position while also providing a pleasant scent within the passenger compartment of the automobile. Fastening components may secure a mobile device to the mobile device holder. Additionally, the removable cap of the mobile device holder and air freshener may allow scented material to be easily replaced when older scented material has lost efficacy.

In some other examples, the mobile device holder and air freshener may include USB ports powered by a car cigarette lighter socket, which may be used to charge or power a mobile devise held by the mobile device holder and air freshener. In another example, the mobile device holder and air freshener may include a fan powered by a solar cell, and may avoid the inconvenience or having to replace batteries.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
a body, wherein the body is arranged so as to include an interior that is at least partially hollow;
a removable cap, wherein the removable cap is removable from the body to allow scented material to be installed within the interior, and the removable cap is distinct from the fragrance material;
a fastening component, wherein the fastening component is effective to secure a mobile electronic device to the apparatus;
a flexible arm coupled to the body at a first end of the flexible arm; and
a mount attached to a second end of the flexible arm, wherein the mount and flexible arm are effective to support the body and the mobile electronic device, and the flexible arm is effective to adjust a position of the body and the mobile electronic device with respect to the mount; and
wherein the body is further arranged so as to allow air that has entered the apparatus through a first vent on a first side of the body of the apparatus to become scented and flow out of the apparatus through a second vent on a second side of the body of the apparatus.

2. The apparatus of claim 1, wherein the apparatus further includes a fan effective to blow air through the apparatus.

3. The apparatus of claim 1, wherein the apparatus further includes an electronic heating device effective to accelerate the release of particulate scented matter from the scented material.

4. The apparatus of claim 1, wherein the mount is effective to secure the apparatus to a surface.

5. The apparatus of claim 4, wherein the mount comprises:
a suction cup; and
a lever, wherein the lever is effective to engage and disengage suction in the suction cup.

6. The apparatus of claim 5, wherein the mount includes a solar cell effective to provide an electric current to the apparatus.

7. The apparatus of claim 1, wherein the fastening component includes a magnet or an adhesive surface.

8. The apparatus of claim 1, wherein the mount is effective to secure the apparatus to a car cigarette lighter socket.

9. The apparatus of claim 1, wherein the mount includes:
an anode electrode;
a cathode electrode; and
a universal serial bus (USB) port, wherein the anode electrode and the cathode electrode align and connect to electrodes of a car cigarette lighter socket and provide a current to the USB port.

10. An apparatus comprising:
a body, wherein the body is arranged so as to include a first interior that is at least partially hollow;
a removable cap, wherein the removable cap is removable from the body to allow scented material to be installed within a second interior of the removable cap, and the removable cap is distinct from the fragrance material;
a fastening component, wherein the fastening component is effective to secure a mobile electronic device to the apparatus;
a flexible arm coupled to the body at a first end of the flexible arm; and
a mount attached to a second end of the flexible arm, wherein the mount and flexible arm are effective to support the body and the mobile electronic device, and the flexible arm is effective to adjust a position of the body and the mobile electronic device with respect to the mount; and
wherein the removable cap is further arranged so as to allow air that has entered the apparatus through a first vent on a first side of the body of the apparatus to become scented through interaction with the scented material.

11. The apparatus of claim 10, wherein the mount is effective to secure the apparatus to a surface.

12. The apparatus of claim 11, wherein the mount comprises:

a suction cup; and a lever, wherein the lever is effective to engage and disengage suction in the suction cup.

13. The apparatus of claim 12, wherein the mount includes a solar cell effective to provide an electric current to the apparatus.

14. The apparatus of claim 10, wherein the fastening component includes a magnet, a piece of metal to which a magnet is attracted, or an adhesive surface.

15. The apparatus of claim 10, wherein the apparatus further includes a fan effective to blow air through the apparatus.

16. The apparatus of claim 10, wherein the mount includes:

an anode electrode;

a cathode electrode; and a universal serial bus (USB) port, wherein the anode electrode and the cathode electrode align and connect to electrodes of a car cigarette lighter socket and provide a current to the USB port.

17. A method to release fragrance from a scented material, the method comprising:

placing the scented material inside an interior of an air freshener apparatus, wherein a fastening component of the air freshener apparatus is configured to secure a mobile electronic device to the air freshener apparatus;

securing the air freshener apparatus onto a surface or a vehicle cigarette lighter socket by a mount attached to a first end of a flexible arm, wherein a second end of the flexible arm is coupled to a body of the air freshener apparatus, and the flexible arm is effective to adjust a position of the body and the mobile electronic device with respect to the mount;

powering a fan with an electric current, wherein the electric current is provided from the mount;

causing air to blow through the air freshener apparatus, by the fan, so that the air passes through a first vent into the air freshener apparatus, wherein particulate matter from the scented material is effective to mix with the air to create scented air; and causing, by the fan, the scented air to blow out of a second vent of the air freshener apparatus.

18. The method of claim 17, wherein the mount includes an anode electrode, a cathode electrode, and a universal serial bus (USB) port, and the anode electrode and the cathode electrode align and connect to electrodes of the car cigarette lighter socket and provide the electric current to the USB port and the fan.

19. The method of claim 17, wherein the mount includes a suction cup, a lever, and a solar cell, wherein the lever is effective to engage and disengage suction in the suction cup and the solar cell is effective to provide the electric current to the fan.

20. The method of claim 19, wherein the apparatus is secured to a windshield of a vehicle.

\* \* \* \* \*